(12) United States Patent
Bornstein (10) Patent No.: US 7,470,124 B2
(45) Date of Patent: Dec. 30, 2008

(54) INSTRUMENT FOR DELIVERY OF OPTICAL ENERGY TO THE DENTAL ROOT CANAL SYSTEM FOR HIDDEN BACTERIAL AND LIVE BIOFILM THERMOLYSIS

(75) Inventor: Eric Bornstein, Natick, MA (US)

(73) Assignee: Nomir Medical Technologies, Inc., Waltham, MA (US)

( * ) Notice: Subject to any disclaimer, the term of this patent is extended or adjusted under 35 U.S.C. 154(b) by 109 days.

(21) Appl. No.: 10/821,442

(22) Filed: Apr. 9, 2004

(65) Prior Publication Data

US 2004/0224288 A1    Nov. 11, 2004

Related U.S. Application Data

(60) Provisional application No. 60/468,944, filed on May 8, 2003.

(51) Int. Cl.
*A61C 5/00*    (2006.01)
(52) U.S. Cl. .............................. 433/29; 433/224; 606/16
(58) Field of Classification Search .................. 433/29, 433/224, 215; 606/13, 15, 16
See application file for complete search history.

(56) References Cited

U.S. PATENT DOCUMENTS

| | | | |
|---|---|---|---|
| 4,669,466 A | | 6/1987 | L'Esperance |
| 4,917,084 A | | 4/1990 | Sinofsky |
| 4,945,239 A | | 7/1990 | Wist et al. |
| 4,979,900 A | * | 12/1990 | Okamoto et al. ............. 433/224 |
| 5,174,297 A | * | 12/1992 | Daikuzono .................. 600/476 |
| 5,196,004 A | | 3/1993 | Sinofsky |
| 5,300,067 A | * | 4/1994 | Nakajima et al. ............. 606/16 |
| 5,324,200 A | * | 6/1994 | Vassiliadis et al. .......... 433/224 |
| 5,374,266 A | * | 12/1994 | Kataoka et al. ............... 606/15 |
| 5,464,436 A | | 11/1995 | Smith |
| 5,503,559 A | * | 4/1996 | Vari ........................... 433/224 |

(Continued)

FOREIGN PATENT DOCUMENTS

JP    2002017757 A    *    1/2002

(Continued)

OTHER PUBLICATIONS

PCT International Search Report for related PCT Application No. PCT/US04/20520 (4 pages).

(Continued)

*Primary Examiner*—Ralph A. Lewis
(74) *Attorney, Agent, or Firm*—John M. Garvey; Foley & Lardner LLP (57) ABSTRACT

A system and process for thermolytic eradication of bacteria and biofilm in the root canal of a human tooth involve an elongated and flexible optical probe and a laser oscillator that provides the probe with low infrared energy. The optical probe is sufficiently long for insertion into substantially the entire length of the root canal of the tooth. The optical probe causes lateral dispersion of the radiation from the probe throughout the root canal. The radiation is provided at an energy density and for a period of time that are necessary to selectively target bacteria and live biofilm in the dentinal tubules of an entire root canal system, at once, thereby (1) inhibiting creation of a blackbody "hot tip", and (2) inducing laser interstitial thermotherapy (LITT) within the root-canal space.

32 Claims, 2 Drawing Sheets

U.S. PATENT DOCUMENTS

| | | | |
|---|---|---|---|
| 5,595,568 | A | 1/1997 | Anderson et al. |
| 5,622,501 | A * | 4/1997 | Levy .......................... 433/215 |
| 5,683,380 | A | 11/1997 | Eckhouse |
| 5,693,043 | A | 12/1997 | Kitterell et al. |
| 5,735,844 | A | 4/1998 | Anderson et al. |
| 5,741,247 | A * | 4/1998 | Rizoiu et al. ................... 606/10 |
| 5,853,407 | A | 12/1998 | Miller |
| 5,897,314 | A * | 4/1999 | Hack et al. ..................... 433/29 |
| 5,954,710 | A | 9/1999 | Paolini |
| 5,968,039 | A * | 10/1999 | Deutsch et al. ................ 606/17 |
| 5,971,755 | A * | 10/1999 | Liebermann et al. .......... 433/29 |
| 6,015,404 | A | 1/2000 | Altshuler et al. |
| 6,080,146 | A | 6/2000 | Altshuler et al. |
| 6,090,788 | A | 7/2000 | Lurie |
| 6,104,959 | A | 8/2000 | Spertell |
| 6,149,644 | A | 11/2000 | Xie |
| 6,162,052 | A * | 12/2000 | Kokubu ....................... 433/29 |
| 6,235,016 | B1 | 5/2001 | Stewart |
| 6,273,884 | B1 | 8/2001 | Altshuler et al. |
| 6,283,986 | B1 | 9/2001 | Johnson |
| 6,387,089 | B1 | 5/2002 | Kreindel et al. |
| 6,508,813 | B1 | 1/2003 | Altshuler et al. |
| 6,514,243 | B1 | 2/2003 | Eckhouse et al. |
| 6,517,532 | B1 | 2/2003 | Altshuler et al. |
| 6,605,080 | B1 | 8/2003 | Altshuler et al. |
| 6,648,904 | B2 | 11/2003 | Altshuler et al. |
| 6,662,054 | B2 | 12/2003 | Kreindel et al. |
| 6,679,837 | B2 * | 1/2004 | Daikuzono ................... 600/157 |
| 6,702,808 | B1 | 3/2004 | Kreindel |
| 6,815,209 | B2 | 11/2004 | Baeummer et al. |
| 6,824,542 | B2 | 11/2004 | Jay |
| 6,878,144 | B2 | 4/2005 | Altshuler et al. |
| 6,887,261 | B1 | 5/2005 | Peyman |
| 6,889,090 | B2 | 5/2005 | Kreindel |
| 6,890,346 | B2 | 5/2005 | Ganz et al. |
| 6,902,563 | B2 | 6/2005 | Wilkens et al. |
| 6,939,344 | B2 | 9/2005 | Kreindel |
| 6,960,201 | B2 | 11/2005 | Cumbie |
| 7,041,100 | B2 | 5/2006 | Kreindel |
| 7,060,061 | B2 | 6/2006 | Altshuler et al. |
| 7,118,563 | B2 | 10/2006 | Weckwerth et al. |
| 2003/0023284 | A1 | 1/2003 | Garstein et al. |
| 2003/0208249 | A1 | 11/2003 | Chen |
| 2004/0093042 | A1 | 5/2004 | Altshuler et al. |
| 2004/0210276 | A1 | 10/2004 | Altshuler et al. |
| 2005/0065577 | A1 | 3/2005 | McArthur et al. |
| 2005/0075703 | A1 | 4/2005 | Larsen |
| 2005/0107853 | A1 | 5/2005 | Krespi et al. |
| 2006/0004425 | A1 | 1/2006 | Cumble |
| 2006/0200213 | A1 | 9/2006 | McDaniel |

FOREIGN PATENT DOCUMENTS

| | | |
|---|---|---|
| WO | WO 91/13652 | 9/1991 |
| WO | WO 01/74265 | 10/2001 |
| WO | WO 02/086550 | 10/2002 |
| WO | WO 03/049892 | 6/2003 |
| WO | WO 03/079883 | 10/2003 |
| WO | WO 03/086215 | 10/2003 |
| WO | WO 2004/000150 | 12/2003 |
| WO | WO 2004/024144 | 3/2004 |
| WO | 2004/058352 | 7/2004 |
| WO | WO 2004/058352 | 7/2004 |
| WO | WO 2006/076506 | 7/2006 |

OTHER PUBLICATIONS

PCT Written Opinion of the International Searching Authority for related PCT Application No. PCT/US04/20520 (4 pages).

J.W. Costerton, et al., Biofilms, the Customized Microniche, Journal of Bacteriology, American Society for Microbiology, Apr. 1994, pp. 2137-2142, vol. 176, No. 8.

A. Mjör, et al., The Density and Branching of Dentinal Tubles in Human Teeth, Archs Oral Biol., Elsevier Science Ltd., , 1996, pp. 401-412, vol. 41, No. 5, Printed in Great Britain.

S. Socransky, et al., Dental Biofilms: Difficult Therapeutic Targets, Periodontology, 2000, pp. 12-55, vol. 28, Printed in Denmark.

P.N. Ramachandran Nair, et al., Persistent Periapical Radiolucencies of Root-Filled Human Teeth, Failed endodontic Treatments, and Periapical Scars, 1999, pp. 617-627, vol. 87, No. 5.

F.H. Takeda, et al., A Comparative Study of the Removal of Smear Layer by Three Endodontic Irrigants and Two Types of Laser, International Endodontic Journal, 1999, pp. 32-39.

A. Moritz, et al., Lasers in Endodontology, Journal of Oral Laser Applications, 2001, pp. 87-95, vol. 1, No. 2.

N. Gutknecht, et al., A Clinical Comparison of the Bactericidal Effect of the Diode Laser and 5% Sodium Hypochlorite in Necrotic Root Canals, Journal of Oral Laser Applications, 2002, vol. 2, No. 3, pp. 151-157.

A. Moritz, et al., Irradiation of Infected Root Canals with a Diode Laser In Vivo: Results of Microbiological Examinations, 1997, Rapid Report, 6 pp.

S. Grant, et al., Degradation-Induced Transmission Losses in Silica Optical Fibers, Laser in Surgery and Medicine, 1997, vol. 21, pp. 65-71.

Liang, et al., Wavelength Dependence of Cell Cloning Efficiency after Optical Trapping, Biophy.J. Mar. 1996, pp. 1529-1533, vol. 70.

Neuman, et al., Characterization of Photodamage to *Escherichia coli* in Optical Traps, Biophy J. Nov. 1999, pp. 2865-2863, vol. 77.

Neuman, K.C., Single Molecule Study of RNA Polymerase Transcription Under Load, Ph.D. Dissertation presented to Princeton University, Nov. 2002, 120 pp.

Karu, et al., Effects of Near-Infrared Laser and Superluminous Diode Irradiation on *Escherichia coli* Division Rate, IEEE Journal of Quantum Elect, Dec. 1990, vol. 26, No. 112.

* cited by examiner

INSTRUMENT FOR DELIVERY OF OPTICAL ENERGY TO THE DENTAL ROOT CANAL SYSTEM FOR HIDDEN BACTERIAL AND LIVE BIOFILM THERMOLYSIS

CROSS REFERENCE TO RELATED APPLICATIONS

The present application is based upon and claims the benefit of the filing date of U.S. provisional application No. 60/468,944, filed 08 May 2003.

STATEMENT REGARDING FEDERALLY SPONSORED RESEARCH OR DEVELOPMENT

Not Applicable

BACKGROUND OF THE INVENTION

1. Field of the Invention

The present invention relates to a system and process for the thermolytic eradication of bacteria and biofilm in the human body, and, more particularly, to the treatment of apical periodontitis in and around the dental structure of endodontically involved teeth.

2. Description of the Prior Art

Various laser and fiber delivery systems have been proposed for the express purpose of disinfecting or sterilizing tissues in a three-dimensional root canal system. Generally, such systems are limited to unidirectional energy delivery or to the generation of a blackbody incandescent "hot tip" at the distal end of an optical delivery fiber path. Such delivery of energy occurs when an unclad "naked" fiber tip comes in contact with tissue and fluid in root canal space. In this instance, debris will accumulate on the tip immediately, and this debris will absorb the intense infrared laser energy propagating through the associated optical delivery fiber. This occurrence will cause the tip to heat and to carbonize immediately. As the energy from the infrared laser photons continue to be absorbed by this newly carbonized tip, the tip will become red hot (above 726° C.). This secondary emission of the "hot tip" energy conducted to the dentinal tubules is accompanied by undesired local thermal and photo-biologic events in the oral tissues and fluids (including blood), i.e. unwanted melting and charring of dental tissues in proximity to the distal end of the delivery fiber. Hence, there is a need in the endodontic art for improving treatment of bacterially fueled inflammatory diseases by effectively destroying live biofilm and bacteria without harming healthy dental or other peripheral tissues.

SUMMARY OF THE PRESENT INVENTION

The primary object of the present invention is to provide, for the thermolytic eradication of bacteria and biofilm in the root canal of a human tooth, a system and process that involve an elongated and flexible optical probe and a laser oscillator that provides the probe with low infrared energy. Preferably, the optical probe is composed of a member of the class consisting of sapphire and zirconium, and has an optically diffusive surface that disperses optical energy throughout 360° laterally of the optical probe and along the entire length of the optical probe. Preferably, the low infrared energy lies within range of 700 nm to 1100 nm and the optical probe is sufficiently long for insertion into substantially the entire length of the root canal of the tooth. The optical probe causes lateral dispersion of the radiation from the probe throughout the root canal. The radiation is provided at an energy density and for a period of time that are necessary to selectively target bacteria and live biofilm in the dentinal tubules of an entire root canal system, at once, thereby (1) inhibiting creation of a blackbody "hot tip", and (2) inducing laser interstitial thermotherapy (LITT) within the root-canal space. The primary optical energy is distributed simultaneously along the entire root canal system to produce 360 degree three dimensional scattering. This permits the use of lower energies and longer treatment times, without creating a blackbody "hot tip". The results are an absence of melting and charring in the root canal space and other benefits to be described below.

BRIEF DESCRIPTION OF THE DRAWINGS

For a fuller understanding of the nature and objects of the present invention, reference is made to the following specification, which is to be taken in connection with the accompanying drawings, wherein.

EXPLANATION AND DESCRIPTION OF THE PREFERRED EMBODIMENT

Current Model for Infected Root Canal Space and Apical Periodontitis

When a vital dental nerve (pulp) becomes infected with pathogenic microorganisms, it undergoes a process of irreversible pulpitis. This occurs when the local inflammatory products and tissue damage, from the bacterial infiltration, cause the dental pulp to succumb and die. This cascade then turns into a frank micro-abscess within the pulp chamber and the accompanying dental root canal three-dimensional structure. As the infection progresses, the entire soft-tissue of the dental pulp undergoes a process of liquefaction necrosis. Within the hard dental canal structure, there results a complete lack of collateral circulation and, subsequently, insufficient drainage available for the necrotic inflammatory fluids within the root canal space. The inflammatory bacteria laden fluids then escape the root canal system at the root apex, and begin to cause a massive inflammatory response at the periapex in the richly vascular periodontal ligament tissues. The periapex is the most inferior anatomical area of the dental root, and contains apical root cementum, periodontal ligament, and alveolar bony tissues. This area is richly impregnated with blood vessels, lymphatics, and nerve fibers. Hence, an infection in the dental canal structure or root canal system will have immediate and profound immunological and inflammatory effects on the surrounding periapical tissues. Even though the bacteria are in direct proximity to the highly vascularized periodontal epithelium, they will continue to grow and thrive, because of their constantly available reservoir in the infected root canal space.

The highly vascularized nature of the periodontal ligament allows for the production and local diffusion of far more than adequate numbers of immunological and inflammatory products by the host to inhibit further bacterial colonization and intrusion into the periapical space. These immunological and inflammatory products include lysozyme, complement, bradykinin, thrombin, fibrinogen, antibodies and lymphocytes.

However, the root canal laden reservoir of bacteria will survive this onslaught and continue to grow in this unique anaerobic environmental niche, which is the infected root canal system. These bacteria will continue to seed the periapical space and fuel the periapical infection, until either the tooth is lost, or successful root canal therapy is completed. The former scenario is known as chronic apical periodontitis.

When intense inflammation of periapical tissues occurs, it most likely will stimulate bone resorption activities through osteoclastic cellular upregulation. If the affected area is left untreated for any length of time, a radiolucent area will appear around the root apex as the infection spreads and the bony architecture breaks down. This occurs as an acute periapical abscess, and is the result of the rapid spread of bacteria and inflammatory byproducts from the root canal system into the surrounding bony architecture of the periapex space. If untreated, this localized infection can cause sever sequelae, including acute osteitis (bone infection) and cellulitis (soft tissue infection) of the affected area.

Traditional treatment of these lesions, in the hope of salvaging the offending tooth, has been removal of the periapical irritants and their living source, by complete debridement of the root canal space, and timely careful obturation of the root canal space with an apical seal. If completed sucessfully, this root canal therapy will allow the periapical tissues to heal by initially forming a fibrin clot. This fibrin clot will then become granatulation tissue, and ultimately mature into new bony architecture and periodontal ligament.

The absolute goal of all endodontic therapy is to completely seal the three-dimensional area of the root canal system. If the seal is correctly accomplished, the offending tooth can be returned to proper comfort and function after the periapical areas have healed and regenerated.

Dentinal Tubule Morphology

The dentin in a tooth is composed of millions of dentinal tubules (small hollow fluid filled tubes in the dentin) running from the dental pulp to just before the dentin-cementum-junction of the tooth root. These tubules are characterized by a diameter of approximately 1 to 3 microns, and run a generally straight course from the pulp to the dentin-cementum junction throughout the entire architecture of the dental root structure. The amount of dentinal tubules present in a tooth per square millimeter has been calculated at anywhere from 4,900 to 90,000 (Mjor and Nordahl, 1996).

The bacteria that infect the dental pulp and ultimately cause pathologic disease in the root canal system are predominantly gram-negative anaerobes. Thirty years ago, in a novel study using injectable silicone, Davis (Oral Surg Oral Med Oral Path, 1972) showed clearly that the complexity, morphology, and architecture of the root canal system is such that even well prepared canals contain areas inaccessible to conventionally used endodontic debridement methods. In fact, Sen and Pi'kin (Endod Dent Traumatol, 1995) found that once a dental pulp is infected, pathogenic bacteria can be recovered in all areas throughout the canal system of a tooth, including the dentinal tubules.

Many investigators have shown that pathogenic bacteria are present in the dentinal tubules of infected teeth half way between the infected canal walls and the dentin-cementum junction. Bacterial penetration also has been described as invading 150 microns into the dentinal tubules in the apical two thirds of the roots, with bacterial endotoxins present within the dentinal walls. An in vitro study by Perez and Rochd (1993) found that laboratory innoculated teeth can have bacterial penetration up to 737 microns into the dentinal tubules.

The dentinal tubular system presents a perfect ecological niche for pathogenic endodontic bacteria. The tubules are at a constant temperature (37° C.), with perfect humidity and readily available nutrients to sustain growth and replication. One of the most virulent and resistant organisms in conventional root canal treatment is the gram-positive organism *Enterococcus faecalis*. *Enterococcus faecalis* is a facultative anaerobe that shows resistance to many antibiotics, intracanal medicaments, and oxygen producing irrigants (Sundqvist; Oral Surg Oral Med Oral Path 1998).

Modern Root Canal Therapy Considerations

Modern root canal therapy consists of removal of the bacteria and diseased pulp tissue from the three-dimensional root canal system of the tooth prior to canal obturation and establishment of an apical seal with gutta percha. To remove the diseased pulp tissue and bacteria in preparation for the obturation phase, a controlled mechanical and chemical series of events (cleaning, shaping, and disinfection) must take place. It is a given that the root canal system in the tooth generally has a very complex geometry, which can have many curves in a single canal. To adequately negotiate this complex geometry, a wide variety of hand instruments (files) and rotary instruments (powered with low speed handpieces) have been developed and brought into use for the initial cleaning and shaping steps in endodontic procedures. These endodontic instruments are flexible and have inherent metal memory properties to aid in the cleaning and shaping protocol of the curved three-dimensional root canal architecture. These instruments can be used successfully with either the "step-back" approach or the "crown down" approach to mechanical root canal debridement. This important step of thorough debridement of the root canal system traditionally has been accomplished mechanically as described above, and will leave behind a "smear layer" of organic and calcified debris on the canal wall surfaces.

The second part of a successful modem root-canal procedure involves the chemomechanical debridement of the three-dimensional root canal system with an irrigant sodium hypochlorite (NaOCl) at a 5% solution. Sodium hypochlorite has been shown in many studies to have the capability to dissolve much of the remaining organic substrates and remove loose superficial debris in the root canal system (Svec and Harrison. J Endod 1977). Sodium hypochlorite offers the dental practitioner many advantages as an endodontic irrigating solution. In addition to flushing the canal area, it is a potent antimicrobial and has tissue-dissolving properties.

However, it is also common knowledge that endodontic irrigating solutions such as sodium hypochlorite may not be able to penetrate the entire length of the root canal system. Many of the anatomical complexities of the root canal system, including the length of the dentinal tubules may be left untouched by the irrigant, and hence may leave live biofilm and bacteria in the area. This is caused primarily by surface tension of the irrigant on the root canal walls, and is a primary source of root canal failure. Orstavik and Haapasalo found (Endod Dent Traumatol 1990) that the antimicrobial effect of NaOCl can only be guaranteed up to a distance of 100 microns in dentine.

Thus. the human root canal system has a wide variety of anatomical complexities, many of which go undiagnosed and subsequently untouched by endodontic files or irrigants. This oversight ultimately can lead to endodontic failure. Because of this complexity, and the inability of a root canal file, rotary instrument, or NaOCl irrigant to reach and clean all aspects of a three-dimensional canal system, it has been virtually impossible to achieve complete destruction and/or removal of all pathologic bacteria and live biofilm within an infected tooth.

Much evidence and clinical experience supports the finding that the residual bacteria in an instrumented, irrigated and prepared but un-obturated canal space can multiply to their original numbers within 2 to 4 days of a cleaning and shaping procedure. As a result of this rapid multiplication of residual bacteria, many investigators have recommended the use of an intracanal medication (such as CaOH paste) between root canal visits to the endodontist. However, most of the currently used intracanal medications show limited benefits as antibacterials, possible antigenic activity, and poor diffusion into the dentinal tubules that are harboring remaining bacteria.

Endodontic Bacterial Pathogens as a Living Biofilm

This survival of bacteria in the dentinal tubules is now known to occur because recent research has newly defined and clearly recognized most bacterial colonies as part of a protected living biofilm. (Darveau, and Tanner et al, The Microbial Challenge in Periodontitis, Periodontology 2000 and Chen; Periodontitis as a biofilm infection, J Calif Dent Assoc. 2001.)

Costerton and Lewandowski, J Bacteriology (1994), have described biofilm as "matrix enclosed bacterial populations adherent to each other and/or to surfaces or interfaces". The same researchers have also described biofilm as "ecological communities that have evolved to permit survival of the community as a whole", with "nutrient channels in the biofilm matrix (a primitive circulatory system) to facilitate the movement of metabolic wastes within the colony". If dentinal tubules and the three-dimensional canal structure within an infected tooth become the ecological niche described above, and their hidden bacterial colonies then are viewed as a living biofilm, more effective management techniques need to be delineated and performed to rid the hidden anatomical complexities of the root canal system of these microbial pathogens.

Current understanding of biofilm has recognized in them some basic properties (Marsh and Bradshaw, Physiological approaches to the control of oral biofilm, Adv Dent Res 1997). These include, but are not limited to, community cooperation between different types of microorganisms, distinct microcolonies within the biofilm matrix, a protective matrix surrounding the bacterial colonies, different distinct microenvironments within different microcolonies, primitive communication systems, and unique protection from and resistance to antibiotics, antimicrobials, and the immunological and inflammatory host response.

Most previous attempts to control endodontic diseases have been performed on the basis of an understanding of endodontic bacteria in laboratory situations. As a living biofilm, however, endodontic bacteria act and function quite differently from what the classical laboratory models would predict. Endodontic bacteria in a biofilm produce different and more harmful chemicals and enzymes than they do in culture. Also, within a biofilm, there is an increase in the spread of antibiotic resistance through inter-species relationships. The biofilm (a protienacious slimy matrix) itself serves as an effective barrier of protection from many therapeutic regimens targeted at the bacteria alone. Antimicrobials and intra-canal medicaments may fail even to penetrate the biofilm and to reach the causative bacteria if they are neutralized by resistant enzymatic reactions within the biofilm. With this new understanding of the endodontic disease paradigm, novel and heretofore untried procedures can be created to combat hidden dentinal tubule bacteria and the recalcitrant biofilm that may harbor and protect the pathogenic bacteria.

The previously explained classical approaches to the treatment of endodontically involved teeth have limitations that ultimately can lead to reinfection and continued progression of the disease.

New Logic for Complete Endodontic Bacterial Debridement

If one thinks of a biofilm as similar in physical character to raw egg albumin, the difficulty in eradicating it with metal files or rotary instruments alone can be easily understood. It would be virtually impossible to clean a broken egg from a ceramic floor with metal instruments by scraping and filing alone. Some of the slimy protienacious albumin would invariably be left behind.

If one is dealing with a live biofilm, the slimy matrix that is left behind in deep dentinal tubules (after mechanical and chemical debridement), will contain surviving bacteria, and with these surviving bacteria, the biofilm, will re-grow in a matter of a few hours. Current medical thought is trying to address the fact that there are apparently areas of the three-dimensional root canal system that are inaccessible to the dental practitioner for mechanical and chemical debridement, and hence continue to be colonized by the living biofilm and pathogenic bacteria. This is why live biofilm targeting with a flexible laser dispersion tip specifically tailored for intracanal bacterial and biofilm thermolytic is necessary in practice.

With live biofilm targeting in the three-dimensional endodontic canal and dentinal tubules, these classical endodontic mechanical and chemical debridement techniques can now be augmented and brought forward into a new dimension with controlled low infrared laser thermolytic. With our greater understanding of endodontic infections and hidden dentinal tubular bacteria as living biofilm, this residual slimy protienacious matrix, with all of the bacterial and host inflammatory and destructive enzymes present in the dentinal tubules and root canal system, can be completely inactivated with the scattered delivery of controlled low infrared optical energy. With the local conversion of this optical energy to heat, the biofilm is coagulated (like an egg in a frying pan) as the laser photons penetrate the entire length of the dentinal tubules after they exit the specially tailored root canal optical dispersion tip of the present invention.

By delivering this optical laser energy after mechanical cleaning and shaping has taken place, any biofilm, bacteria and harmful enzymes remaining in the dentinal tubules will take on the new physical form of a denatured and inactive solid coagulum. Live biofilm thermolytic can be used as an adjunct to root canal therapy after the mechanical and chemotherapeutic protocols are completed. Laser augmentation presents a novel approach to seek out and target previously inaccessible areas of the root canal system for endodontic treatment and to concurrently kill living biofilm remaining in the tubules as it is transformed into a denatured and inactive solid coagulum.

It has been established in the prior art that laser debridement in conjunction with mechanical cleaning and shaping of the canal space is an effective adjunctive treatment modality to classic endodontic treatment of an infected tooth. Previously, however, the procedures of the prior art have been difficult to accomplish and fraught with problems.

Description of Prior Art Laser Root Canal Debridement

The question asked of lasers in the field of endodontics has always been, "Can a laser provide improved treatment outcomes over the conventional classical methods?" There currently are a few laser systems approved for adjunctive root canal therapy by the United States Food and Drug Administration. Even so, the acceptance of laser use for endodontic therapy has remained limited. This is due to the inherent problems of unidirectional optical energy delivery within the confines of the root canal space. Mechanical cleaning and shaping of the root canal space is a primary goal of classical endodontics. Only mid infrared lasers that can actually ablate (cut) dentine efficiently can be used for this purpose, in the place of root canal files. To date, only erbium lasers (mid infrared ablative lasers have been approved for this procedure. However, when compared to classical mechanical debridement, ablation rates with the mid-infrared lasers are slow, and the beam can only exit the delivery tip in one direction (either vertically or horizontally). Also, as Erbium lasers have the highest available coefficient of absorption for the chromophore of water, the beam of such a laser will penetrate only 2 to 10 microns per pulse into the dentin. This is a far shorter distance than the 750 micron penetration of residual bacteria in dentinal tubules.

Ablation of root canal dentin is not the focus or the desired outcome of the present invention. Once the three-dimensional canal structure is classically prepared, Takeda (Int Endod J 1999) found that the smear layer can be removed and the dentin melted by the heat generated by a laser. In the prior art, many studies have been completed using Nd:YAG lasers (1064 nm) and conventional dental diode lasers (800 nm) to thermally kill bacteria and seal the canal surface by delivering the optical energy through a small flexible optical fiber. For laser energy to be deemed effective in bacterial thermolytic within the dentinal tubules, it is of primary importance that the optical energy actually penetrates into the whole root surface through the dentin. There have been promising studies finding that even though the intensity of the optical energy is weakened the farther it penetrates into the dentin, a bactericidal effect is maintained up to a depth of 1 mm (1000 μm) (Kline, J Clin Laser Med Surg 1997). Now if the above logic is coupled to the findings that dentinal tubules act as optical energy conductors (miniature waveguides) (Odor; Int Endod J 1996) and laser radiation can negatively effect gram-positive and gram-negative bacteria in the distal aspects of root-canals (Moritz; Lasers Surg Med 2000), the efficacy of laser use in endodontic bacterial and biofilm thermolytic becomes clear.

In the earlier generation of laser delivery devices, it was very difficult if not impossible to deliver optical energy to the apical third of the root canal system. With new optical flexible fibers, laser energy can be delivered directly into the root canal system and to the apical third of the root.

The lasers that are ideal for this function with maximum penetration value in the target tissue are the near infrared lasers from 800 nm to 1064 nm. The fiber delivery of the previous art, however, has presented a series of problems that were not overcome. A common theme in all aspects of photobiology is the fact that power densities per unit time, and per unit area, directly influence the type of laser/tissue interaction that occurs. As the high intensity laser energy is absorbed by the dentin (tissue target), it is transformed into local heat energy, due to the photothermal interaction. Within normal parameters of the previous art of root canal laser debridement with Nd:YAG or 800 nm diode lasers, there was a tremendous density of optical energy being delivered from the small unit area of the 200 or 400 micron optical fiber tip, as the tip carbonized in the root-canal space, and melted the proximal dentine along with thermally necrosing adjacent bone. The following is a description of these unwanted quantum and thermal interactions.

General Photobiology of Near-Infrared Laser Energy

Niemz (Laser-Tissue Interactions. Fundamentals and Applications, Berlin, Springer, pp45-80, 2002) has determined that all effects with near-infrared laser wavelengths at pulse durations of 1 microsecond or greater are thermal in nature. There are 5 factors to consider regarding heat generation by these lasers:

(1) Wavelength and optical penetration depth of the laser;
(2) Absorption charactistics of exposed tissue;
(3) Temporal mode (pulsed or continuous);
(4) Exposure time; and
(5) Power density of the laser beam.

The first parameter of near-infrared diode lasers that must be understood is the penetration depth of the optical energy. Diode lasers in the near infrared range have a very low absorption coefficient in water, hence they achieve deep optical penetration in tissues that contain 80% water (including the oral mucosa and dentinal tubules). This means that, for a conventional dental diode soft tissue laser, the depth of penetration per pulse is estimated to be greater than that of the Er:YAG hard tissue laser by a factor of $10^4$. The short wavelengths of the near-infrared diode and Nd:YAG lasers have very high absorption peaks in molecules (chromophores) such as melanin and hemoglobin, along with dark pigmented bacteria. This will allow the laser energy to pass with minimal absorption through water, producing thermal effects much deeper in the tissue (up to 4 cm) as the photons are absorbed by these pigments and pass through the water. This photobiology allows for controlled deeper soft-tissue coagulation and propagation in and through the dentinal tubules.

The next parameter to bear in mind is the heat effect in the tissue being irradiated, based on the pulse mode of currently available near-infrared systems. Presently, for dental treatment, near-infrared lasers either emit photons in the continuous wave (CW) or gated continuous wave (Gated CW) pulsed mode for diode systems, or free running pulsed mode (FRP) for Nd:YAG lasers. This fact is very important in practice because the duration of the tissue exposure to the photon energy of the laser will govern the thermal tissue interaction that is achieved.

In the CW or Gated CW mode, laser photons are emitted at one single power level, in a continuous stream. When the stream is gated, there is an intermittent shuttering of the beam by a mechanical gate that is positioned in the path of the beam, essentially turning the laser energy on and off. The duration of an on and off cycle in this type of laser system is generally on the order of milliseconds, and the "power-per-pulse" stays at the average power of the CW beam. Nd:YAG lasers, in the FRP mode, can produce very large peak energies of laser energy, for extremely short time intervals on the order of microseconds.

As an example, one of these lasers with a temporal pulse duration of 100 microseconds, with pulses delivered at ten per second (10 Hz), means that the laser photons are hitting the tissue for only $\frac{1}{1000}$th of a second (total time) and that the laser is "off" for the remainder of that second. This will give the tissue significant time to cool before the next pulse of laser energy is emitted. These longer intervals between pulses will benefit the thermal relaxation time of the tissue. The CW mode of operation will always generate more heat than a pulsed energy application.

If the temporal pulses are too long (or the exposure in CW is too long), the thermal relaxation effect in the tissues is overcome and irreversible damage to non-target areas may occur. If adequate cooling and appropriate exposure times are practiced, these problems will be prevented. So, not only the ultimate temperature reached in the tissue interaction with the laser energy is of concern, but also the temporal duration of this temperature increase plays a significant role for the induction of desired tissue effects, and the inhibition of irreversible tissue damage. For nanosecond and picosecond pulses (that today's dental lasers cannot achieve), heat diffusion during the laser pulse would be negligible.

The power density of the beam is determined by the peak power generated by the laser, divided by the area of the focused beam. This means that the smaller the diameter of the fiber used to deliver the energy (200 µm, 400 µm, 600 µm), and the closer the fiber is to the tissue (i.e., a smaller "spot size", without touching the tissue), the greater the power density (amount of emitted photons per square mm of the beam) and the greater the thermal interaction. With a non-contact "clean" fiber tip, the two most important considerations are the spot size of the beam, and the distance of the fiber tip to the tissue. When the dental near-infrared lasers are used in the "contact mode" with a "hot-tip" fiber (i.e. all root canal applications), the energy delivery, and hence the photobiology, will substantially change.

In addition to being the means to deliver laser photons to a target tissue, the silica fibers at the tip of the diode laser device can act as a "hot tip" cutting or melting device, if the tip becomes carbonized, i.e. "activated". When an activated, unclad fiber tip comes in contact with tissue and fluid (as it will if it is placed is placed in a dental nerve canal), debris will immediately accumulate on the tip. This debris will absorb the intense infrared laser energy propagating through the fiber, which will cause the tip to heat and immediately carbonize the tissue detritus. As the energy from the infrared laser photons continue to be absorbed by this newly carbonized tip, the tip will become red hot (temperatures above 726° C.). Grant, S. et al, Degradation-Induced Transmission Losses in Silica Optical Fibers, Lasers in Surgery and Medicine, 21:65-71 (1997). Once this occurs, the tip of the fiber (having become a "black body radiator") will generate a secondary visible optical emission as it becomes incandescent and glows. As more photons from the near infrared dental laser continue to bombard the black, carbonized tip and are absorbed by the organic debris, there is a rapid increase in temperature at the tip. (Kuhn, T: Black Body Theory and the Quantum Discontinuity, 1894-1912, Chicago, The University of Chicago Press, 1978) and (plank, M: The Theory of Heat Radiation, New York, Dover Publications Inc. 1991)

It is this intense heat of the carbonized and glowing fiber tip that is known as the "hot tip" for diode laser procedures. With this "hot tip" in the dentinal tubules, the photobiology and laser-tissue interaction is profoundly different from what is found when using a non-carbonized and non-contact fiber that emits only the primary emission, near-infrared photons. In the prior art, these realities (i.e. "hot tip) fibers cannot be overcome, and must be clearly understood by the practitioner so that safe and predictable root-canal procedures can be realized with these lasers.

Photobiology of "Hot Tips" and Black Body Radiators.

To understand the thermodynamic and photobiologic ramifications of the intense heat and subsequent carbonization of the fiber tip, a short review of how black solids absorb and then reemit electromagnetic energy will be useful. In the mid 1800's, Gustav Kirchoff observed that "a hot opaque substance emits a continuous spectrum of radiation." He observed that black solid objects "glow" and emit light when heated. This phenomenon is referred to as "blackbody emission". In 1900, Max Plank, by examining the available experimental data concerning the emission of heat and light from high temperature solids, described and revealed some fundamental rules of Quantum Mechanics (Black Body energy release arises from thermal radiation and thermal excitation of atoms). Dentists using diode lasers in the contact mode, in the root canal space, can now appreciate a few of the quantum realities about the "hot tips" (blackbodies) that they are using as part of the root-canal process.

(1) Theoretically, a blackbody is an object that absorbs all light. (ie the carbonized tip absorbs a large percentage of the infrared photons being emitted from the laser.)

(2) As the carbonized tip continues to absorb laser photons, it heats up. (i.e. the longer the laser is firing into the "hot tip", or the higher the output energy, the hotter the tip will be)

(3) The energy and peak wavelength of emitted photons depends on the temperature of the tip. (i.e. The hotter the tip becomes, the more total light, infrared, visible, and ultraviolet, will be emitted from the tip.)

(4) The heated tip emits light (photons) in a continuous spectrum at infrared, visible, and ultraviolet wavelengths. (i.e. No longer just the single infrared wavelength from the primary emission of the laser.)

(5) Hotter objects are brighter at all wavelengths.

Photobiology Differences with Contact "Hot Tips"

As stated, in contact mode a large percentage of the near-infrared photons (the primary emission of the laser) are absorbed by the blackbody tip and carbonized coagulum causing a "Hot Tip". Therefore, the size of the resulting coagulation zone associated with the tip is dependent on the exposure time of the "hot tip" to the dentinal tubules and tissues, and the heat conduction from the tip to these tissue. These greatly decreased primary emissions of the laser through a carbonized tip were studied in detail by Grant et al, (Degradation Induced Transmission Losses in Silica Optical Fibers, Lasers in Surgery and Medicine, 21:65-71 (1997)) as they specifically looked at the "fiber interaction" during contact laser surgery. Grant showed that with tissue deposits at the tip of the fiber absorbing larger amounts of laser light, immediate carbonization occurs.

The carbonization of the fiber tip leads to an increase in temperature, and this can result in significant damage to the optical quality of the fiber (the temperature spikes to greater than 9000 C). They also found that, once the carbonization of the tip occurs, the tip no longer functions as an adequate light guide. The laser will no longer adequately photocoagulate with primary photons, but rather it will incise and cauterize the tissue because of the intense heat at the tip.

It is important to remember that the glass portion of an optical transmission fiber consists of two regions: the core that runs through the center of the strand, and the cladding that surrounds the core. The cladding has a different refractive index than the core, and acts as a reflector that causes the laser light to reflect back into the core during its transmission through the fiber. Furthermore, longer lasing times and higher power drastically reduces the forward power transmission of the laser radiation, as the fiber tip sustains more and more heat induced damage.

When testing a 360 micron fiber with a 830 nm diode laser at 3 watts CW, the inventor hereof (testing with a laser power meter) found that an immediate 30% loss of forward power transmission occurs with fiber carbonization from tissue detritus. Further loss was observed as the irradiation period of time continued and tissue debris accumulated.

This phenomenon was examined in vivo by Willems and Vandertop. Contact laser assisted neuroendoscopy can be performed safely using pretreated 'black' fibre tips, experimental data being provided in Lasers Surg Med. 2001;28(4): 324-9. Using diode and Nd:Y AG lasers, conventional fiber tips and coated fiber tips were compared for ablation efficiency in rabbit cerebral tissue. With the conventional fiber tips, histology and thermal imaging demonstrated deleterious effects deep into the tissue. When using the coated fiber tip, they reported that almost all laser light was transformed into thermal energy (as the tip carbonized), and instantly produced ablative temperatures at the tip itself. Further, they reported that ablation was observed at low energy and power (1 watt for 1 second) with thermal effects restricted only to the superficial structures.

This restriction of thermal effects to superficial structures appears to be the consequence of attenuation of the forward power transmission of the laser radiation when a larger percentage of the primary emissions of the laser are absorbed by the tip. As a result, optical transmission qualities are damaged. Also of significance, as the quality of the fiber transmission diminishes as a result of damage to the tip, the energy, focus, and homogeneity of the energy being transmitted from the tip is affected. The primary energy that is still available for forward power transmission out of the tip is far less efficient for tissue penetration and photocoagulation. These are the important and fundamentally different biological consequences associated with diode lasers in the contact or non-contact modes in the current art.

In fact, based on these quantum heat interactions at the diode delivery tips, and because of this (high energy density) issue, an international standard has been set for the prior art. This standard specifies that, with this prior art, the diode laser fiber could not be left at the apical stop of the tooth for more than one second without a critical rise in temperature that would irreversibly injure the healthy periapical structures. That is a difficult standard to uphold and keep. Below are the standard international settings for the dental diode and Nd:YAG lasers when used for root canal debridement.

| INTERNATIONAL STANDARD SETTINGS | |
|---|---|
| Diode Laser | Nd:Y AG Laser |
| –2.5 Watt | –1.5 Watt |
| –15 Hz | –15 Hz |
| –5 Sec | –5 Sec |

The prior art calls for the following method of application. After conventional mechanical and chemical preparation of the tooth undergoing endodontic therapy, the canal space is well dried with sterile paper points. The opening of the root-canal is enlarged to a minimum of ISO 30 so that the optical fiber can be inserted and bent into the canal space without friction to the apical stop. This limitation is intended to prevent fiber breakage. Once the laser is activated, the practitioner can remain at the apical stop only for a period of one second to prevent a critical rise in temperature and irreversible damage to the periapical tissues. After this one second irradiation is accomplished, the activated laser fiber is moved in a rotating fashion from the apical to the coronal portion of the tooth to attempt to reach all of the internal dentinal structure. Once this is accomplished, the root canal space is sealed with gutta percha in a conventional manner. It is recommended that this treatment take place three times over the course of three weeks to accomplish adequate bacterial thermolytic before obturation with the gutta percha. The applicable steps of the aforementioned prior art procedure can be practiced more effectively than ever with the instrument and process of the present invention.

DETAILED DESCRIPTION OF THE PREFERRED EMBODIMENT

Figure 1:
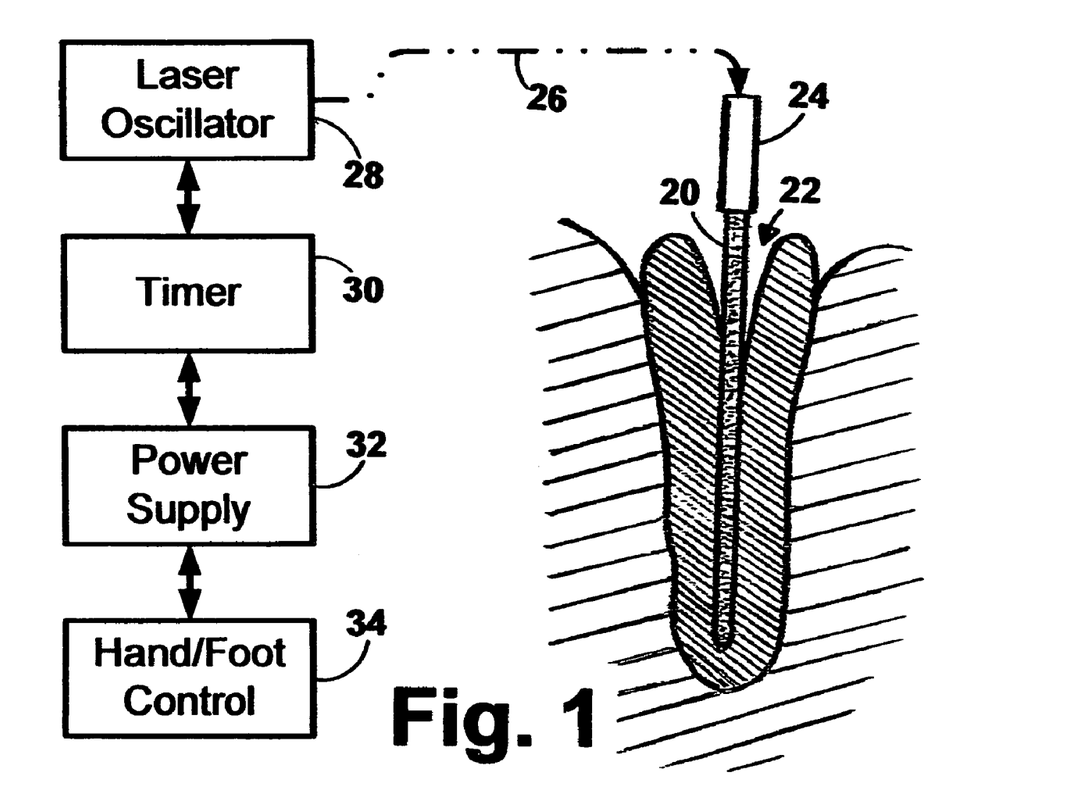
FIG. 1 illustrates a novel laser structure as used in a root canal procedure according to the present invention.
Figure 2:
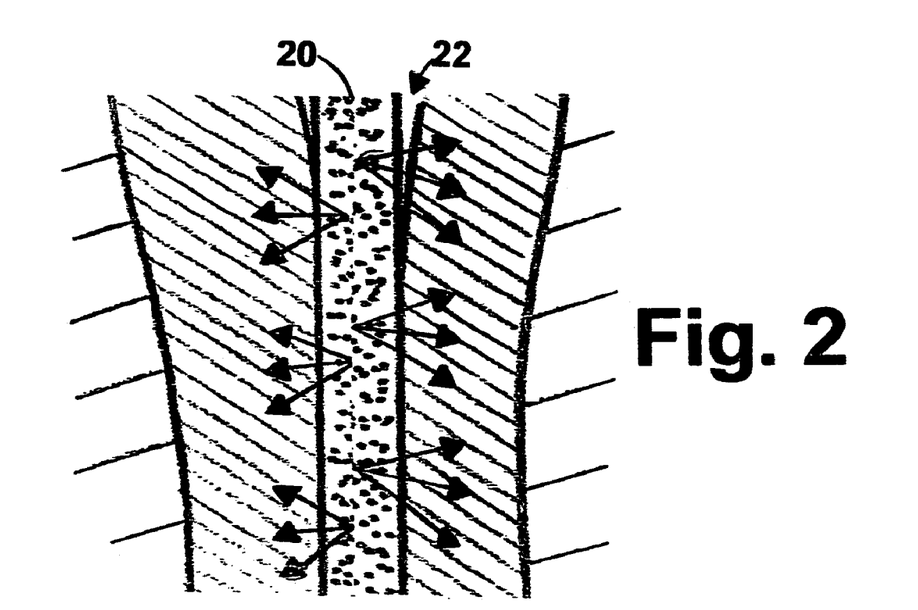
FIG. 2 is an enlarged broken-away view of the structure of FIG. 1, showing the diffuse emission of laser energy into surrounding tissue.

The system of FIGS. 1 and 2.

With reference to FIGS. 1 and 2, the present invention provides a specialized flexible optical delivery probe 20 for use in a process that may be called laser augmented root-canal interstitial thermotherapy ("LARIT").

This probe facilitates the thermolytic eradication of bacteria and biofilm in the root canal 22 of a human tooth. Operatively connected to the probe via an optical adaptor 24 are an optical cable 26, a laser oscillator 28, a timer 30, a power supply 32, and a hand/foot control 34.

Preferably, the optical probe is composed of a member of the class consisting of sapphire and zirconium, and has an optically diffusive surface that disperses optical energy throughout 360° laterally of the optical probe and along the entire length of the optical probe; the optical fiber ranges in diameter between 400 to 1000 μ; the optical probe ranges in diameter from ISO 20 to ISO 70; the laser oscillator generates radiation in the low infrared wavelength range of 700 nm to 1100 nm; the optical fiber is operatively connected between the laser oscillator and an ingress at the proximal end of the optical probe. The design is such that the optical probe is sufficiently long for insertion into substantially the entire length of the root canal of the tooth, and causes dispersion of the radiation from the probe throughout the root canal for dispersion of the radiation at an energy density and for a period of time that are necessary to destroy bacteria and biofilm throughout the root canal system.

The laser root-canal probe has a diffusive surface to cause lateral emission of scattered optical energy along the entire length of the probe. In one embodiment the surface is roughened. In another embodiment the surface is frosted. This structure enables the following distinct physical characteristics in the optical energy that is delivered to the dentin in the root canal system.

In one form, probe 20 is tapering or conical. As indicated above, it scatters the near infrared photons radially along the entire span of the altered tip surface in 360 degrees. With this tapering or conical frosted sapphire or zirconium dispersion probe, there is a uniform and predictable dosage of near infrared optical energy to effect biofilm thermolytic within the tri-dimensional root canal space and dentinal tubules, by which there is conversion of photons to localized heat. The illustrated dispersion phenomenon (of the photons) is discussed generally by H. Fujii et al, "Light Scattering Properties of a Rough-ended Optical Fibre", Optica and Laser Technology, February 1984, pp. 40-44.

In the illustrated embodiment, the outer surface of the root canal interstitial thermal-therapy probe is textured, to provide for a ground glass effect, or a frosted effect, and to allow for and enhance the side delivery or scattering of the near infrared laser photons. In effect, the probe creates a linear diffuser or radiator. The probe itself is input mode independent. That is, the distribution of light out of the diffuser is independent of the coupling mode. With the above described instrument, it is possible to distribute the illuminating optical near infrared energy evenly throughout the tri-dimensional root canal system, in order to effect the bacterial and biofilm thermolytic.

(1) The controlled use of radially emitted primary laser photons along the entire longitudinal length of the probe throughout the entire tridimensional structure of the root-canal system 22, including the dentinal tubules, is possible while the probe is stationary within the root canal.

(2) The diffusive surface of the probe enables scattering of optical energy throughout the entire longitudinal length of the probe when seated in the root canal structure, while controlling the time during which contiguous tissue is subjected to the radiation.

(3) There is no concentration of high density optical energy that might burn or melt dental or periapical tissue due to lack of precise execution of the therapy in practice. Specifically, "blackbody" formation is inhibited.

(4) The dental practitioner is permitted to use a simple continuous wave laser mode, so that the use of lower the laser energies is possible, and the treatment time can be extended, thereby extending the margin of safety for collateral tissues.

The procedure avoids harm to collateral tissues and to healthy periodontal architecture. The main concern is avoidance of a critical rise in temperature in the periapical tissues and/or the external root surface connected to the periodontal ligament and bone. If either area were to experience a temperature rise of 10° C. for more than one minute, periodontal ligament necrosis, tooth ankylosis, and or root resorption might occur. (Eriksson; J Prosthet Dent 1983.)

The Therapeutic Window of Opportunity

To accomplish safe and predictable bacterial cell death and live biofilm thermolytic with near infrared dental lasers, the operator must be cognizant of the very narrow therapeutic window afforded by the lasers' thermal interactions with human tissues. Normal human temperature is 37° C., which corresponds to a rapid bacterial growth curve in the dentinal tubules. When radiant optical energy is applied to the oral tissues with a near infrared dental laser, the temperature of the lazed area starts to rise immediately. Each 10° C. rise in tissue temperature carries an injurious biological interaction with the tissue. At 45° C., the remaining soft tissue becomes hyperthermic. At 50° C., there is reduction in cellular enzyme activity and some cell immobility. At 60° C., there is a denaturation of cellular proteins and collagen with the beginnings of coagulation. At 80° C., there is a permeabilization of cell membranes. And at 100° C., there is vaporization of water and biological matter. If there is any significant duration of time that the temperature increase is at or beyond the 80° C. mark (5 to 10 seconds) at the peri apex or periodontal ligament structure surrounding the root of the tooth, there is irreversible and unwanted harm to the bone, periodontal and dental structures.

To achieve photothermolysis (heat induced death) and live biofilm coagulation with the near infrared dental diode laser, a significant temperature increase must occur for a given amount of time in the target tissue and dentinal tubules. For most of the infectious oral flora, growth will continue almost unabated until the surrounding dentinal tubules reach a temperature of 50° C. At this temperature, the bacterial growth curve begins to slow down.

At 60° C., most bacterial growth comes to a halt except for possible thermophiles in the system. From 60° C. to 80° C. is the range of temperature that is generally accepted in a time dependent manner for any significant bacterial, death and live biofilm coagulation to occur. The prerequisite, for the live biofilm phase shift to occur from a slimy protienacious matrix to a solid coagulumis, is the achievement of this thermal range (60° C. to 80° C.) in the tissue and tissue area for short periods of time, under skilled control and delivery. This prequisite must occur for the near infrared dental laser to be effective at bacterial thermolytic without causing undue harm to healthy oral tissues. The key reqirement is avoidance of a critical temperature rise in the peripheral soft tissue areas of the tooth to. With the laser augmented root canal optical dispersion tip of the present invention, this is now possible.

The following bacteria being targeted for thermolytic in accordance with the present invention are those specifically involved endodontic infections. The endodontic infectious bacteria include, but are not limited to: *Fusobacterium, Peptostreptococcus, Eubacterium, Prevotella, Lactobacillus, Streptococcus, Bacteroides, Enterococcus, Actinomyces,* and *Propionibacterium.*

Figure 3:
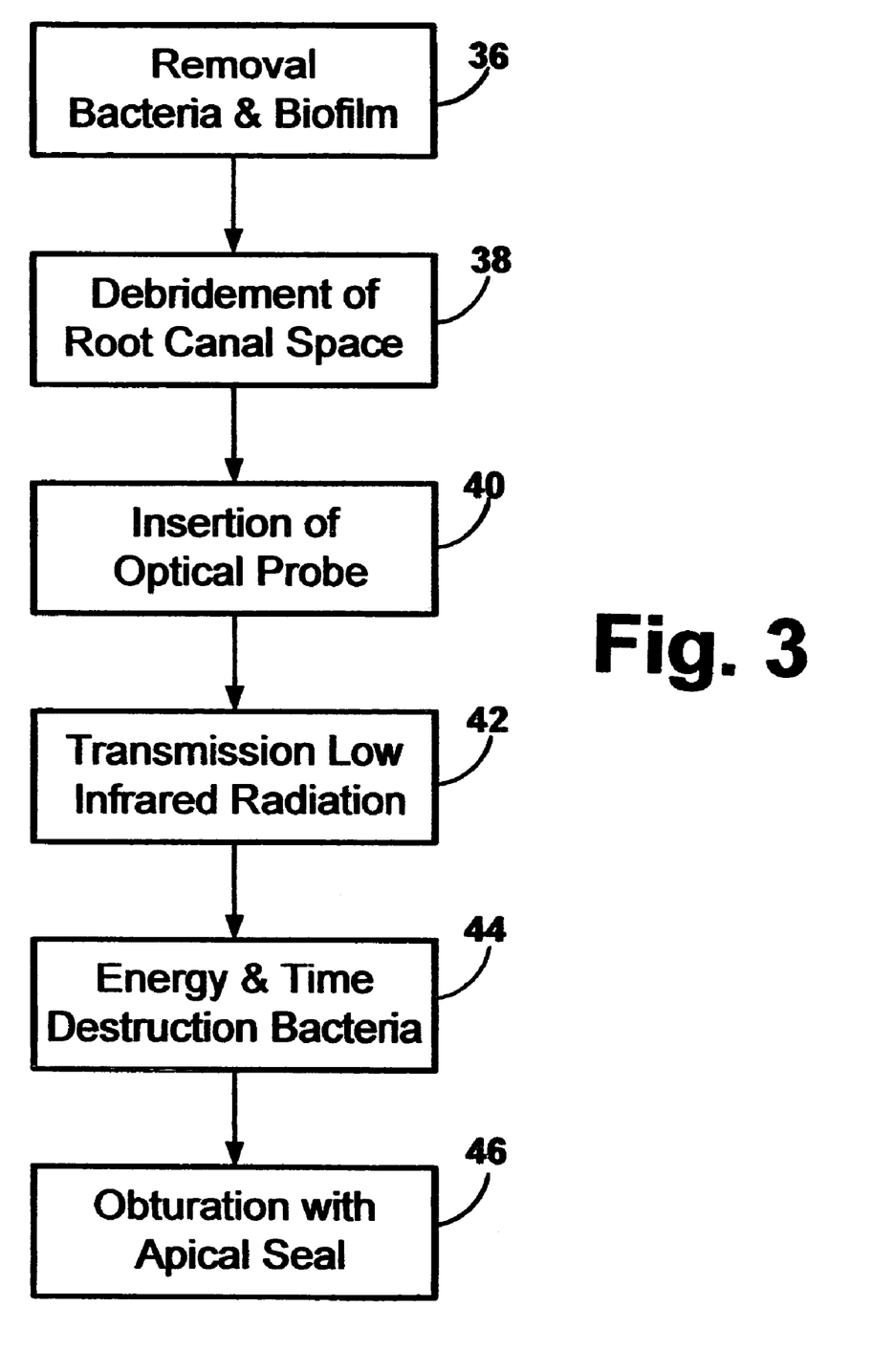
FIG. 3 is a flow diagram of a process involving the present invention.

The Therapeutic Procedure of FIG. 3

A process for treatment of the root canal of a human tooth is depicted in FIG. 3, as comprising the steps of: removing, as at 36, the of bacteria and biofilm from the entire elongated space of a root canal; debridement, as at 38, of the entire elongated space; insertion, as at 40, of an elongated optical probe into the entire elongated space; transmission, as at 42, of low infrared radiation longitudinally into the entire length of the optical probe and laterally through the surface of the elongated probe and into the surface of the root canal walls; the transmission being of sufficient energy density and sufficient time duration to destroy remnants of the bacteria and biofilm in and adjacent to said root canal; and obturation, as at 44, of the root canal space with an apical seal.

The basic laws of thermodynamics state that the exchange and transfer of energy needs to happen in at least two ways, with one of the ways being heat transfer. The heat deposition from the absorption of optical infi'ared energy exploited in this invention is to be used specifically as an adjunctive method for bacterial elimination and live biofilm coagulation in the tridimensional root canal space.

Solid state diode and Nd:YAG lasers in the low infrared spectnun 600 nm to 1100 nm will be used for this purpose because of their preferential penetration curve in the dentinal tubules without an ablative effect. Because of the poor absorption in water of this spectrum of infrared radiation, the penetration of the radiant energy in biological tissues is profound as it can reach over 3 cm. (Nimetz, M. Photobiology 2002). These characteristics of poor absorption to the chromophore of water and deep penetration in the tissues make it an excellent spectrum for the present invention's unique need. Because of these unique characteristics, the near infrared laser energy being delivered from the laser augmented root canal dispersion tip to the dentinal tubules accomplishes its goal of seeking out and targeting bacteria and live biofilm anywhere within the tridimensional root canal space for coagulation and elimination.

This photothermolysis works well with many of the conventional low infrared dental lasers currently on the market. Such dental lasers are easily available and function at the wavelengths of 810 nm, 830 nm, 980 nm or 1064 nm. Because each of these wavelengths is essentially transparent to the bacteria, photothermolysis and live biofilm coagulation through optical heat conversion is the method by which bacterial death will occur.

Another diode laser applicable to the present invention allows the operator to moderately turn down the power and increase the exposure time even more in the area of treatment, to gain selective bacterial death with or without complete biofilm coagulation. This is a dual wavelength (870 nm and 930 nm) diode laser. This laser is designed to kill bacteria with a photodamage effect instead of a photothermal effect. This effect occurs because the wavelengths (870 nm and 930 nm), in selected cases, are not transparent to the bacteria in the live biofilm and lethally react with one or more bacterial intracellular chromophores or pigments to damage the bacterial cell and induce death. This laser when coupled to a root canal dispersion tip penetrates the confines of live biofilm to electively target the pathogenic bacteria more effectively than can any pharmacological or mechanical method. The dual laser requires even less energy than other conventional low infrared lasers and further expands the therapeutic window against the bacteria. Since it is already selectively targeting bacterial chromophores, it kills the bacteria by photodamage along with the photothermolysis and coagulation.

OPERATION

The present invention thus provides an instrument and method that expand the therapeutic window of opportunity currently available with conventional dental solid state diode and Nd:YAG lasers. This near infrared laser energy is dispersed through the optical root canal tip to thermally coagulate live biofilm and to kill bacteria in a simple and predictable manner without harming the adjacent dental structures.

The instrument and process of the present invention are adapted for use with the the laser systems currently owned by many dental professionals, which typically operate in the near infrared with a wavelength ranging from 800 nm to 1064 nm.

A large number of such laser laser systems in the infrared spectrum have been used to kill pathogenic bacteria in dentistry and medicine. The ultraviolet spectrum also has been used to attack bacterial DNA and kill the bacteria. However, many ultraviolet wavelengths also have deleterious effect on human tissue. Dentistry, for the last few years, has used near infrared solid state diode and Nd:YAG lasers for tissue cutting, cautery, and bacterial thermolytic. The four most widely used dental near infrared wavelengths are 810 nm, 830 nm, 980 nm, and 1064 nm. These near infrared lasers have a very low absorption curve in water, and hence, have a very deep tissue penetration curve. Because these wavelengths are almost transparent to most oral flora, there is no direct chromophore targeting of the organisms, and bacterial death is wholly a function of heat deposition to the bacteria and live biofilm from the local conversion of optical energy to heat from the laser. This heat deposition follows the path of optical absorption, and hence, excess power or energy density in the endodontic laser procedure can induce heat related deleterious effects to the patient.

Near infrared dental lasers have been used to kill oral pathogens specifically in the endodontic tissues and treat inflammatory endodontic disease. This was attempted even before dental science had a clear understanding of live biofilm and optical photon dispersion through frosted optical delivery tips. With all procedures of this nature, it has been found that there is a distinct time dependent therapeutic window of opportunity and safety. This narrow window exists because of the intense and deep delivery of infrared optical energy produced by the manufactured mechanics and inherent thermodynamics of the traditional near infrared dental laser delivery systems. Prior art delivery has always been through the distal end of a 200 or 400 micron optical fiber.

As the above logical progression demonstrates, the laser augmented root canal dispersion tip of the present invention can be used with, and coupled to, any existing low infrared laser that a practitioner may already have.

Laser Induced Interstitial Thermotherapy

Laser induced interstitial thermotherapy ("LITT") involves thermal mechanical phenomena dealing with the destruction of different volumes of human or animal tissue in a disease or tumor site. To accomplish LITT, the temperature of the tissue involved is elevated above a given threshold temperature for a given duration of time by the selective absorption of laser photons. These photons are transmitted to the tissue via an optical fiber conditioned to scatter and diffuse the optical energy within the tissue. The fibers used for transmitting this optical energy may be termed interstitial thermotherapy fibers (ITT), and are generally protected from the heat of the target tissue via a glass sleeve. An unprotected fiber may significantly rise in temperature with tissue detritus and coagulum to a point where it melts or fractures.

It is the intention of the present invention to use the scientific principles of LITT in a flexible roughened synthetic sapphire (or other heat resistant optical material) tip connected to an Nd:YAG or diode laser through a laser fiber connector, to effectively impart the optical energy through scattering and diffusion to the entire tridimensional root-canal system including the dentinal tubules. In this invention, the LITT root-canal tip will be used to effect and coagulate residual bacteria and live biofilm after traditional mechanical and chemical root canal shaping and debridement has taken place.

As indicated above, the purpose of the present invention is expand the therapeutic window of opportunity given by the near infrared dental laser by directly targeting the live biofilm and pathogenic bacteria with a specially designed LITT flexible root canal tip. This tip will be a roughened or frosted synthetic sapphire (or other hardened heat resistant optical material) designed to disperse optical energy to the entire root canal system at once using the principles and logic of LITT. These LITT root canal tips will correspond to sizes ISO 20, 25, 30, 35, 40, 45, 50, 55, 60, 65, 70, and 75. The different lengths of the LITT root canal tips I accordance with the present invention range from 10 mm to 40 mm.

By direct live biofilm chromophore targeting with the laser augmented root canal interstitial thermotherapy tip (LARIT) in the prescribed method, the operator of an 810 nm, 830 nm, dual (870 nm and 930 nm), 980 nm, or 1064 nm dental laser can turn down the power and increase the time available for the procedure to gain bacterial death and live biofilm phase change through coagulation and thermolytic. This selective optical energy conversion to heat in the live biofilm and targeted bacteria, causes faster complete bacterial death and coagulation with less energy delivery to the entire system, thereby expanding the therapeutic window of the near infrared dental laser. This leads to a safer procedure for the dental patient, and preserves more collagen, bone, and healthy soft tissue from irreversible thermal damage from the delivery of optical energy.

The laser energy is delivered through a commercially available dental near infrared laser through a surgical fiber from 200 microns to 1000 microns in diameter with a conical tip connected through a proprietary fiber connector to the LARIT apparatus. The laser energy is delivered in a continuous wave or pulsed mode. The laser energy is delivered from 5 to 120 seconds per area while the LARIT apparatus is stationary in the root canal system 1 to 2 millimeters from the apex of the root. The energy production from the laser through the LARIT apparatus is no less than 200 milliwatts and no more than 4000 milliwatts for the duration of the treatment.

The present invention takes advantage of the following critical features and properties of near infrared dental lasers. (1) Widely available near infrared dental lasers now in use have wavelengths in a perfect range for bacterial thermolytic with the above prescribed procedure. (2) The power parameters for use with LARIT, 200 mw to 4,000 mw, are appropriate for use with currently available dental lasers. (3) The processes and products of the present invention are safer and more predicable to use with a near infrared dental laser than traditional dental ablative lasers for bacterial thermolytic and live biofilm coagulation alone.

What is claimed is:

1. A system for the thermolytic eradication of microorganisms and biofilm in the root canal of a human tooth, said system comprising an elongated and flexible optical probe, a laser oscillator communicating with the distal end of said optical probe through at least one optical fiber, a power supply operatively connected to said laser oscillator, and a control operatively connected to said power supply and said laser oscillator;
- (a) said optical probe being composed of a member of the class consisting of sapphire and zirconium, and having an optically diffusive surface dispersing optical energy throughout 360° laterally of said optical probe and along the entire length of said optical probe;
- (b) said optical fiber ranging in diameter between 400 to 1000 μm;
- (c) said optical probe ranging in diameter from ISO 20 to ISO 70;
- (d) said laser oscillator generating radiation in two near infrared wavelengths including about 870 nm and 930 nm, respectively;
- (e) said optical fiber being operatively connected between said laser oscillator and an ingress at the proximal end of said optical probe;
- (f) said optical probe being sufficiently long for insertion into substantially the entire length of the root canal of said tooth;
- (g) said optical probe causing lateral dispersion of said radiation from said probe throughout said root canal; and
- (h) said control being configured and arranged for energizing said laser oscillator for disperation of said radiation at an energy density and for a period of time sufficent to thermolyze said microorganisms and said biofilm in said root canal.

2. The system of claim 1, wherein said period of time is sufficient to destroy pathogenic microorganisms in said root canal.

3. The system of claim 1, wherein said laser oscillator is a diode, and said radiation is continuous mode radiation.

4. The system of claim 1, wherein said laser oscillator is a diode, and said radiation is gated continuous mode radiation.

5. The system of claim 1, wherein said laser oscillator is configured such that said radiation emitted as pulsed mode radiation.

6. A process for treatment of the root canal of a human tooth, said process comprising:
- (a) preliminary removal of bacteria and biofilm from the entire elongated space of said root canal;
- (b) debridement of said entire elongated space;
- (c) insertion of an elongated optical probe into said entire elongated space;
- (d) transmission of low infrared radiation of two wavelengths including about 870 nm and 930 nm, respectively, longitudinally into the entire length of said optical probe and laterally through the surface of said elongated probe to the surface of said root canal defining said space, and through the dentinal tubules adjoining said root canal space;
- (e) said transmission being of sufficient energy density and sufficient time duration to thermolyze said biofilm and destroy remnants of said bacteria and adjacent to said root canal; and
- (g) obturation of said space with an apical seal.

7. The process of claim 6, wherein said optical probe is composed of a member of the class consisting of sapphire and ziconium.

8. The process of claim 6, wherein said optical probe has an optically diffusive surface dispersing optical energy throughout 360° laterally of said optical probe and along the entire length of said optical probe.

9. The process of claim 6, wherein said radiation is transmitted from said laser to said probe via at least one optical fiber ranging in diameter between 400 to 1000 μm.

10. The process of claim 6, wherein said optical probe ranges in diameter from ISO 20 to ISO 70.

11. The process of claim 6, wherein said laser oscillator generates radiation at duel wavelengths including 780 nm and 930 nm, respectively.

12. A process for treatment of an infection in the root canal of a human tooth, said process comprising:
- (a) mechanical and chemical removal of bacteria and biofilm from the elongated space of said root canal;
- (b) mechanical shaping of said elongated space;
- (c) insertion of an elongated optical probe into said elongated space;
- (d) transmission of low infrared radiation longitudinally into the entire length of said optical probe and laterally through the surface of said elongated probe to the surface of said root canal defining said space;
- (e) said transmission being of sufficient energy density and sufficient time duraiton to destroy remnants of said bacteria and biofilm in and adjacent to said root canal; and
- (f) obturation of said space with an apical seal;
- (g) said optical probe being composed of a member of the class consisting of sapphire and zirconium;
- (h) said optical probe having an optically diffusive surface dispersing optical energy throughout 360° laterally of said optical probe and along substantially the entire lenghth of said optical probe;
- (i) said radiation being transmitted from said laser to said probe via at least one optical fiber ranging in diameter between 400 to 1000 μm;
- (j) said optical probe ranging in diameter from ISO 20 to ISO 70; and
- (k) said laser oscillator being configured and arranged for generating radiatoion in two near infrared wavelengths including about 870 nm to 930 nm, respectively.

13. The process of claim 12, wherein the infection includes *Fusobacterium*.

14. The process of claim 12, wherein the infection includes *Peptostreptococcus*.

15. The process of claim 12, wherein the infection includes *Eubacterium*.

16. The process of claim 12, wherein the infection includes *Prevotella*.

17. The process of claim 12, wherein the infection includes *Lactobacillus*.

18. The process of claim 12, wherein the infection includes *Streptococcus*.

19. The process of claim 12, wherein the infection includes *Bacteroides*.

20. The process of claim 12, wherein the infection includes *Enterococcus*.

21. The process of claim 12, wherein the infection includes *Actinomyces*.

22. The process of claim 12, wherein the infection includes *Propionibacterium*.

23. A system for creating a photodamage effect for the eradicaition of microorganisms and biofilm that can be applied for the treatment of a root canal of a human tooth, said system comprising an elongated and flexible optical probe, a laser oscillator communicating with the distal end of said optical probe through at least one optical fiber, a power supply operatively connected to said laser oscillator, and a control operatively connected to said power supply and said laser oscillator;

(a) said optical probe being composed of a member of the class consisting of sapphire and zirconium, and having an optically diffusive surface dispersing optical energy throughout 360° laterally of said optical probe and along the entire length of said optical probe;
(b) said optical fiber ranging in diameter between 400 to 1000 μm;
(c) said optical probe ranging in diameter from ISO 20 to ISO 70;
(d) said laser oscillator generating radiation at two near infrared wavelengths including about 870 nm and 930 nm, respectively;
(e) said optical fiber being operatively connected between said laser oscillator and an ingress at the proximal end of said optical probe;
(f) said optical probe being sufficiently long for insertion into substantially the entire length ot the root canal of said tooth;
(g) said optical probe causing lateral dispersion of said radiation from said probe throughout said root canal; and
(h) said control being configured and arranged for energizing said laser oscillator for dispersion of said radiation at an energy density and for a period of time sufficient to produce a desired photodamage effect in said microorganisms and said biofilm.

24. The system of claim 23, wherein said period of time is suficient to destroy pathogenic microorganisms in said root canal.

25. The system of claim 23, wherein said laser oscillator is a diode, and said radiation is continuous mode radiation.

26. The system of claim 23, wherein said laser oscillator is a diode, and said radiation is gated continuous mode radiation.

27. The system of claim 23, wherein said laser oscillator is configured such that said radiation emitted as pulsed mode radiation.

28. A process for treatment of the root canal of a human tooth, said process comprising:
(a) preliminary removal of bacteria and biofilm from the entire elongated space of said root canal;
(b) debridement of said entire elongated space;
(c) insertion of an elongated optical probe into said entire elongated space;
(d) transmission of low infrared radiation at two wavelengths including about 870 nm and 930 nm, respectively, longitudinally into the entire length of said optical probe and laterally through the surface of said elongated probe to the surface of said root canal defining said space, and through the dentinal tubules adjoining said root canal space;
(e) said transmission being of sufficient energy density and sufficient time duration to produce a desired photodamage effect in said biofilm and destroy remnants of said bacteria in and adjacent to aid root canal; and
(g) obturation of said space with an apical seal.

29. The process of claim 28, wherein said optical probe is composed of a member of the class consisting of sapphire and zirconium.

30. The process of claim 28, wherein said optical probe has an opticall diffusive surface dispersing optical energy throughout 360° laterally of said optical probe and along the entire length of said optical probe.

31. The process of claim 28, wherein said radiation is transmitted from said laser to said probe via at least one optical fiber ranging in diameter between 400 to 1000 μm.

32. The process of claim 28, wherein said optical probe ranges in diameter from ISO 20 to ISO 70.

* * * * *

UNITED STATES PATENT AND TRADEMARK OFFICE
CERTIFICATE OF CORRECTION

PATENT NO.       : 7,470,124 B2
APPLICATION NO.  : 10/821442
DATED            : December 30, 2008
INVENTOR(S)      : Eric Bornstein It is certified that error appears in the above-identified patent and that said Letters Patent is hereby corrected as shown below:

Claim 1, column 17, lines 26-28 currently read as follows:
"(h) said control being configured and arranged for energizing said laser oscillator for disperation of said radiation at an energy density and for a period of time sufficent to"

Please correct Claim 1, column 17, lines 26-28 to read as follows:
-- (h) said control being configured and arranged for energizing said laser oscillator for dispersion of said radiation at an energy density and for a period of time sufficient to --

Claim 2, column 17, lines 31-33 currently read as follows:
"The system of claim 1, wherein said period of time is sufficent to destroy pathogenic microorganisms in said root canal."

Please correct Claim 2, column 17, lines 31-33 to read as follows:
-- The system of claim 1, wherein said period of time is sufficient to destroy pathogenic microorganisms in said root canal. --

Claim 6, column 17, lines 57 and 58 currently read as follows:
"destroy remnants of said bacteria and adjacent to said root canal; and"

Please correct Claim 6, column 17, lines 57 and 58 to read as follows:
-- destroy remnants of said bacteria and in and adjacent to said root canal; and --

Claim 7, column 17, lines 60-62 currently read as follows:
"The process of claim 6, wherein said optical probe is composed of a member of the class consisting of sapphire and ziconium."

Please correct Claim 7, column 17, lines 60-62 to read as follows:
-- The process of claim 6, wherein said optical probe is composed of a member of the class consisting of sapphire and zirconium. --

Claim 11, column 18, lines 6-8 currently read as follows:
"The process of claim 6, wherein said laser oscillator generates radiation at duel wavelengths including 780 nm and 930 nm, respectively."

Please correct Claim 11, column 18, lines 6-8 to read as follows:
-- The process of claim 6, wherein said laser oscillator generates radiation at dual wavelengths including 870 nm and 930 nm, respectively. --

UNITED STATES PATENT AND TRADEMARK OFFICE
CERTIFICATE OF CORRECTION

PATENT NO.       : 7,470,124 B2
APPLICATION NO.  : 10/821442
DATED            : December 30, 2008
INVENTOR(S)      : Eric Bornstein It is certified that error appears in the above-identified patent and that said Letters Patent is hereby corrected as shown below:

Claim 12, column 18, lines 20-22 currently read as follows:
"(e) said transmission being of sufficient energy density and sufficient time duraiton to destroy remnants of said bacteria and biofilm in and adjacent to said root canal; and"

Please correct Claim 12, column 18, lines 20-22 to read as follows:
-- (e) said transmission being of sufficient energy density and sufficient time duration to destroy remnants of said bacteria and biofilm in and adjacent to said root canal; and --

Claim 12, column 18, lines 26-29 currently read as follows;
"(h) said optical probe having an optically diffusive surface dispersing optical energy throughout 360° laterally of said optical probe and along substantially the entire lenghth of said optical probe;"

Please correct Claim 12, column 18, lines 26-29 to read as follows:
-- (h) said optical probe having an optically diffusive surface dispersing optical energy throughout 360° laterally of said optical probe and along substantially the entire length of said optical probe; --

Claim 12, column 18, lines 35-37 currently read as follows:
"(k) said laser oscillator being configured and arranged for generating radiatoion in two near infrared wavelengths including about 870 nm and 930 nm, respectively."

Please correct Claim 12, column 18, lines 26-29 to read as follows:
-- (k) said laser oscillator being configured and arranged for generating radiation in two near infrared wavelengths including about 870 nm and 930 nm, respectively. --

Claim 24, column 19, lines 27-29 currently read as follows:
"The system of claim 23, wherein said period of time is suficient to destroy pathogenic microorganisms in said root canal."

Please correct Claim 24, column 19, lines 27-29 to read as follows:
-- The system of claim 23, wherein said period of time is sufficient to destroy pathogenic microorganisms in said root canal. --

UNITED STATES PATENT AND TRADEMARK OFFICE
CERTIFICATE OF CORRECTION

PATENT NO. : 7,470,124 B2
APPLICATION NO. : 10/821442
DATED : December 30, 2008
INVENTOR(S) : Eric Bornstein It is certified that error appears in the above-identified patent and that said Letters Patent is hereby corrected as shown below:

Claim 28, column 20, lines 18-21 currently read as follows:
"(e) said transmission being of sufficient energy density and sufficient time duration to produce a desired photodamage effect in said biofilm and destroy remnants of said bacteria in and adjacent to aid root canal."

Please correct Claim 28, column 20, lines 18-21 to read as follows:
-- (e) said transmission being of sufficient energy density and sufficient time duration to produce a desired photodamage effect in said biofilm and destroy remnants of said bacteria in and adjacent to said root canal --

Claim 30, column 20, lines 26-29 currently read as follows:
"The process of claim 28, wherein said optical probe has an opticall diffusive surface dispersing optical energy throughout 360° laterally of said optical probe and along the entire length of said optical probe."

Please correct Claim 30, column 20, lines 26-29 to read as follows:
-- The process of claim 28, wherein said optical probe has an optically diffusive surface dispersing optical energy throughout 360° laterally of said optical probe and along the entire length of said optical probe. --

Signed and Sealed this

Fourteenth Day of April, 2009

JOHN DOLL
*Acting Director of the United States Patent and Trademark Office*